(12) United States Patent
Wantink et al.

(10) Patent No.: US 6,991,626 B2
(45) Date of Patent: Jan. 31, 2006

(54) POLYMER JACKET WITH ADHESIVE INNER LAYER

(75) Inventors: Kenneth L. Wantink, Temecula, CA (US); Jeong S. Lee, Diamond Bar, CA (US); Emmanuel C. Biagtan, Temecula, CA (US); Alan A. Tannier, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 34 days.

(21) Appl. No.: 10/264,855

(22) Filed: Oct. 4, 2002

(65) Prior Publication Data

US 2003/0060757 A1    Mar. 27, 2003

Related U.S. Application Data

(63) Continuation of application No. 09/739,180, filed on Dec. 15, 2000, now Pat. No. 6,488,655, which is a continuation-in-part of application No. 09/345,664, filed on Jun. 30, 1999, now Pat. No. 6,193,686.

(51) Int. Cl.
*A61M 25/00* (2006.01)

(52) U.S. Cl. .................. 604/524; 604/103.09
(58) Field of Classification Search ........ 604/191–194, 604/198, 108, 264, 523, 524, 525, 526, 527, 604/530, 531, 533, 534, 535, 103.09; 138/137, 138/141, 140, 174, 177; 600/585, 434; 264/345
See application file for complete search history.

(56) References Cited

U.S. PATENT DOCUMENTS

| | | | |
|---|---|---|---|
| 5,562,127 A | * | 10/1996 | Fanselow et al. ........... 138/137 |
| 5,712,044 A | | 1/1998 | Fanselow et al. |
| 5,797,877 A | * | 8/1998 | Hamilton et al. ......... 604/96.01 |
| 5,911,715 A | * | 6/1999 | Berg et al. .................. 604/525 |
| 6,010,521 A | * | 1/2000 | Lee et al. .................... 606/194 |
| 6,575,958 B1 | | 6/2003 | Happ et al. |

* cited by examiner

*Primary Examiner*—Manuel Mendez
(74) *Attorney, Agent, or Firm*—Fulwider Patton LLP

(57) ABSTRACT

The invention is an elongate intracorporeal member having a polymer jacket secured to a high strength shaft with the polymer jacket having an outer layer of polymeric material and an inner layer formed of polymeric adhesive. In one embodiment, a balloon catheter has a proximal high strength tubular section with a polymer jacket having an polymeric outer layer and an adhesive polymer inner layer. In another embodiment, a guidewire has an elongate core with polymer jacket disposed about at least a portion of the elongate core, wherein the polymer jacket comprises a polymeric outer layer an inner layer of polymeric adhesive disposed between and bonding the outer layer to the elongate core.

6 Claims, 3 Drawing Sheets

POLYMER JACKET WITH ADHESIVE INNER LAYER

RELATED APPLICATIONS

This application is a continuation of Ser. No. 09/739,180, filed Dec. 15, 2000, now U.S. Pat. No. 6,488,655 and a continuation-in-part of U.S. application Ser. No. 09/345,664, filed Jun. 30, 1999 now U.S. Pat. No. 6,193,686, which is hereby incorporated by reference in its entirety.

BACKGROUND OF THE INVENTION

The present invention is directed to elongate intracorporeal devices, and particularly intraluminal devices for stent deployment, percutaneous transluminal coronary angioplasty (PTCA), and the similar procedures that are facilitated by an inflatable tubular member. The invention is also directed to elongated intracorporeal devices, such as guidewires, used for guiding intraluminal devices for stent deployment, PTCA and similar procedures.

PTCA is a widely used procedure for the treatment of coronary heart disease. In this procedure, a balloon dilatation catheter is advanced into the patient's coronary artery over a guidewire and the balloon on the catheter is inflated within the stenotic region of the patient's artery to open up the arterial passageway and increase the blood flow through the artery.

To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced therein until the preshaped distal tip of the guiding catheter is disposed within the aorta adjacent the ostium of the desired coronary artery. The guiding catheter is torqued from its proximal end outside the patient to guide the shaped distal end into a desired coronary ostium. Once the distal end of the guiding catheter is properly seated in the coronary ostium, a balloon catheter may then be advanced through the guiding catheter into the patient's coronary artery over a guidewire until the balloon on the catheter is disposed within the stenotic region of the patient's artery.

Once properly positioned across the stenosis, the balloon is inflated one or more times to a predetermined size with radiopaque liquid at relatively high pressures (e.g., generally 4–12 atmospheres) to dilate the stenosed region of a diseased artery. After the inflations, the balloon is finally deflated so that the dilatation catheter can be removed from the dilated stenosis to resume blood flow.

Similarly, balloon catheters may be used to deploy endoprosthetic devices such as stents which are generally cylindrical shaped intravascular devices. These devices are expanded within a damaged artery to hold the artery open. The device can be used to prevent restenosis and to maintain the patency of blood vessel immediately after intravascular treatments. Typically, a compressed or otherwise small diameter stent is disposed about an expandable member such as a balloon on the distal end of a catheter, and the catheter and stent thereon are advanced through the patient's vascular system in the same manner as described above for dilatation catheters. Inflation of the balloon expands the stent within the blood vessel. Subsequent deflation of the balloon allows the catheter to be withdrawn, leaving the expanded stent within the blood vessel.

The proximal shaft section of a balloon catheter or other percutaneous device will often include a tubular member made from high strength materials such as stainless steel, chromium-cobalt alloys such as MP35N, superelastic NiTi alloys, high strength composite materials or the like. The high strength tubular member gives the proximal shaft section the column strength and pushability required for the device while maintaining an inner lumen of sufficient bore for inflation or deflation of an expandable member disposed at the distal section of the balloon catheter. The high strength tubular members can be susceptible to kinking and breaking while being manipulated through tortuous body channels during use. Also, it can be difficult to bond various polymeric materials to many of these high strength tubular members which complicates the manufacturing process and increases the price of the catheter.

To solve these shortcomings, the high strength tubular member is often jacketed with high strength extruded polymer tubing to provide heat bondable polymeric material on the outside surface of the high strength tubular member in order to more easily secure the member to other components of the catheter. In addition, the high strength extruded polymer jacket material provides added safety to the catheter in the event that the high strength tubular member kinks or breaks inside a patient during a surgical procedure. If the high strength tubular member kinks or breaks while inside a patient during a surgical procedure, the high strength extruded polymer jacket can provide a resilient sheath which is not subject to kinking or breaking that enables the physician to withdraw the catheter from the patient without the need for surgical intervention.

While it is desirable to have a high strength extruded polymer jacket over the high strength tubular member, the jackets usually have to be applied as relatively thick tubular sections in order to prevent them from bulging out from the high strength tubular member when high pressure fluids are injected into the lumen within the proximal shaft section. Such a jacket having a relatively thick wall section can add considerably to the cross sectional area of the proximal shaft of the catheter which reduces the amount of cross sectional area available for the inflation/deflation lumen which can complicate the surgical procedure. What has been needed is a catheter having a proximal shaft section with a high strength tubular member that is jacketed with a high strength extruded polymer jacket with a relatively thin wall section that is not subject to bulging out from the high strength tubular member under high inflation pressures.

Similarly, it is often desirable to provide the core member of a guidewire with a polymer jacket in order to maintain the outer diameter of the guidewire in portions where the core has been distally tapered to provide greater flexibility. A polymer jacket may also provide a desired outer surface texture for a guidewire, including added lubricity to facilitate advancement of the guidewire through a patient's vasculature during a procedure, irrespective of whether the jacket maintains a constant outer diameter.

Thus, what has also been needed is a reliable process for securing a polymer jacket to the outside surface of a metallic portion of an intraluminal devices such as guidewires and catheters.

The present invention satisfies these and other needs.

SUMMARY OF THE INVENTION

The invention is directed to an intracorporeal device which has a polymer jacket securely bonded to a high strength member of the intracorporeal device by a polymeric adhesive.

The intracorporeal devices embodying features of the invention have elongated high strength members with polymeric jackets which are bonded to the surfaces by polymeric adhesives.

In one embodiment, a balloon catheter has an elongate shaft with a proximal section formed at least in part of a high strength tubular member and a polymer jacket disposed about the high strength tubular member. The polymer jacket comprises an outer layer of high strength polymer and an inner layer of an polymeric adhesive polymer disposed between and bonding the outer layer to the high strength tubular member. In another embodiment, a guidewire has an elongate core with a distal section formed at least in part of a high strength member and a flexible polymeric body disposed about the distal section of the elongate core. The flexible polymeric body disposed about at least a portion of the elongate core comprises an outer layer of polymeric material and an inner layer of polymeric adhesive disposed between and bonding the outer layer to the elongate core.

Preferably, the adhesive polymer layer includes an adhesive polymer selected from the group consisting of ethylene acrylic acid copolymer and functionally modified polyolefins. The outer polymeric layer preferably comprises a polymer selected from the group consisting of polyurethane, nylon 12 and a polyether block amide such as PEBAX (which is sold by Elf Atochem).

The invention also comprises methods of securing a polymer jacket to a elongate high strength intracorporeal member, including coextruding a polymer jacket having an polymeric outer layer and a polymeric adhesive inner layer and necking the polymer jacket over the high strength shaft at a temperature above the melting temperature of the adhesive polymer inner layer and below the melting temperature of the polymeric outer layer.

The multilayered jacket secured to the high strength tubular or other elongated member allows for a significant reduction in the thickness of the outer polymer layer, e.g. thickness reductions of up to about 0.002 inch (0.05 mm) or more. These and other advantages of the invention will become more apparent from the following detailed description and the accompanying exemplary drawings.

DETAILED DESCRIPTION OF THE INVENTION

Figure 1:
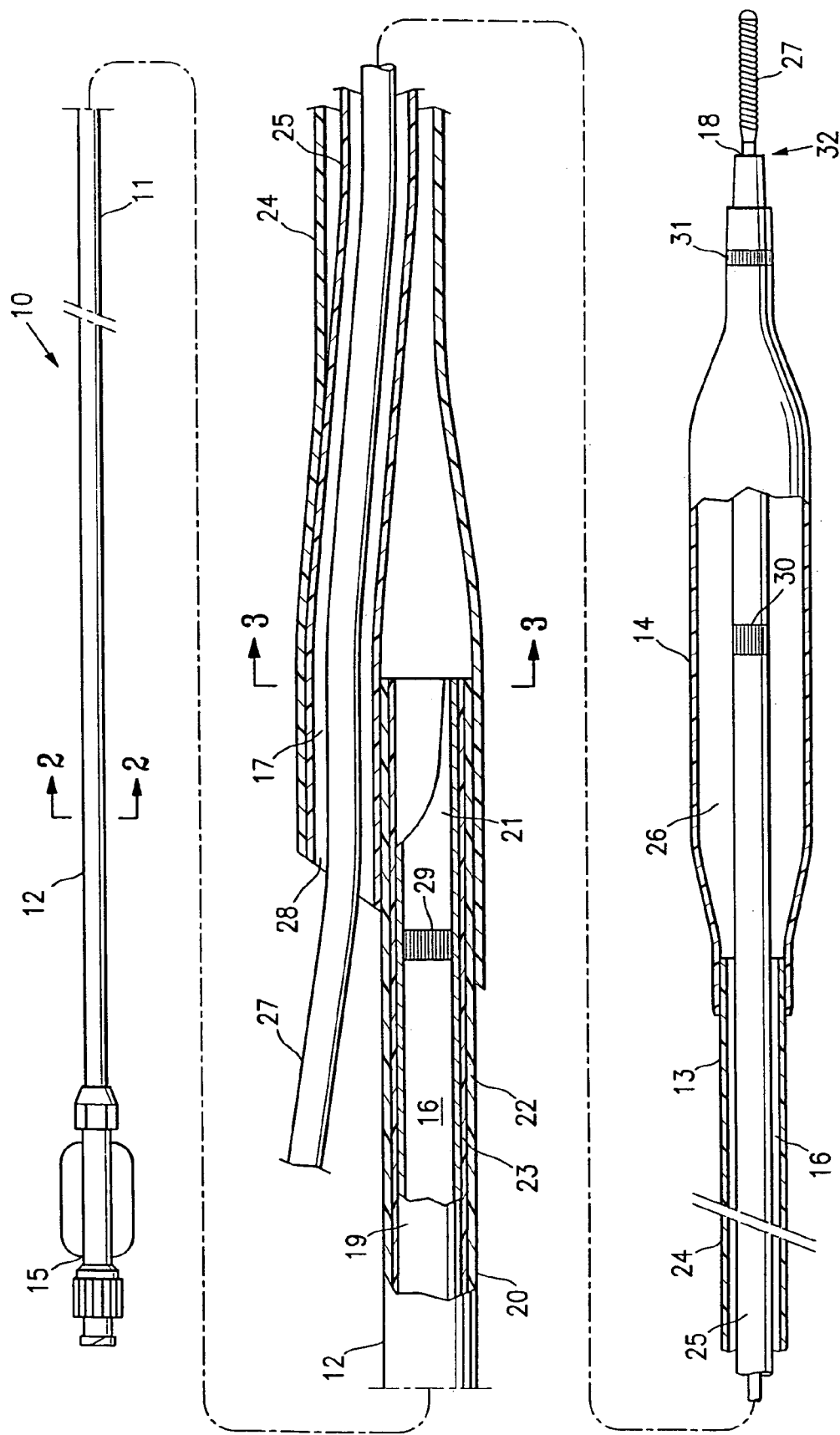
FIG. 1 is a schematic, elevational view, partially in section, of a catheter system embodying features of the invention.
Figure 3:
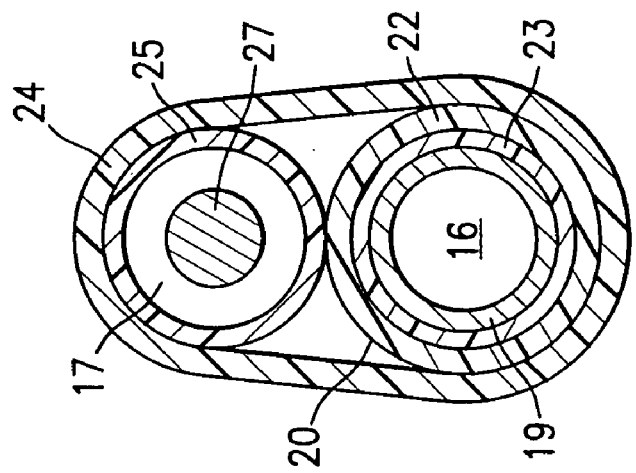
FIG. 3 is a transverse cross sectional view of the catheter system of FIG. 1 taken along lines 3—3.
Figure 2:
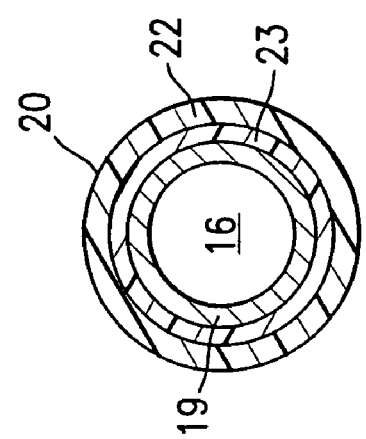
FIG. 2 is a transverse cross sectional view of the catheter system of FIG. 1 taken along lines 2—2.

FIGS. 1–3 illustrate an intravascular catheter 10 embodying features of the invention which generally includes an elongated catheter shaft 11 with a proximal shaft section 12, a distal shaft section 13, and a radially expansive inflatable balloon 14 on the distal shaft section 13. An adapter 15 is shown mounted on the proximal end of proximal shaft section 12. An inflation lumen 16 extends within the catheter shaft 11 from the proximal end thereof to a location spaced proximal to the distal end of the shaft. A guidewire receiving lumen 17 extends within the distal shaft section 13 to port 18 in the distal end of the catheter.

The proximal shaft section 12 is formed of a high strength tubular member 19 with a polymeric jacket 20. The inflation lumen 16 within the proximal shaft section is defined by the tubular member 19 as shown in FIG. 2. The distal tip 21 of the tubular member 19 is tapered distally to smaller transverse dimensions. The tubular member 19 is preferably formed of a high strength material such as 304v stainless steel, NiTi alloy, MP35N, Elgiloy and the like. Non-metallic materials may also be used such as braided polyimide, high strength polymers such as polyetheretherketone (PEEK), polyetherketone, polyketone, and composite materials. The adapter 16 and the nose piece for the adapter may be formed of conventional polymeric materials such as polycarbonate. As used herein reference to a material having high strength shall mean a material having a tensile strength at break of at least 4000 psi (27.6 mpascals), preferably at least 4500 psi.(31 mpascals).

The jacket 20 has a two layered structure, preferably formed by coextrusion, with an outer layer 22 formed of high strength polymeric material to withstand the pressures of inflation fluid and an inner layer 23 of adhesive polymer to securely bond the outer layer to the tubular member 19. In one embodiment, the outer layer 22 is a high strength, neckable polymer such as Nylon 12 (available from EMS American Grilon Inc.) or other suitable polymer capable of withstanding inflation pressures of 300 psi and higher. The inner adhesive layer 23 is formed of an adhesive polymer such as ethylene acrylic acid copolymers (for example, Primacor, available from Dow Plastics) and tie layer resin or functionally modified polyolefins (for example, Plexar, available from Equistar Chemicals) or an adhesive resin such as Bynel from DuPont or Nucral (an ethylene methacrylic acid copolymer) available from DuPont. As used herein, polymeric adhesives refers to polymers that, once secured to the high strength proximal member, cannot be detached with reasonable force, without using tools such as a razor blade. The adhesion between inner layer 23 and high strength proximal member 19 is strong enough to prevent high pressure inflation fluid from separating the outer layer from the high strength tubular member and leading to a blow out when the balloon is inflated. Since the polymeric adhesive prevents the incursion of inflation fluid between the outer layer and the tubular member to which it is bonded, outer polymer layer need not have a thickness sufficient to resist the inflation fluid, allowing either a reduced overall diameter of the catheter or an inflation lumen with an increased diameter, which decreases inflation/deflation times. Reductions of up to 0.002 inch (0.05 mm) or more in wall thickness of the outer layer can be obtained by the use of a suitable polymeric adhesive.

The distal shaft section 13 has an outer tubular member 24 and an inner tubular member 25 disposed within the outer tubular member and defining with the outer tubular member, at least in part, the portion of the inflation lumen 16 extending within the distal shaft section. As best shown in FIG. 3, the portion of the inflation lumen 16 in the distal shaft section is in fluid communication with the interior chamber 26 of the inflatable balloon 14. The distal end of the balloon 14 is secured to the distal end of the inner tubular member 25 and the proximal end of the balloon is secured to the distal end of the outer tubular member 24. These catheter components are preferably bonded by laser bonding which provides a flexible yet sealed bond.

The guidewire lumen 17 extends through the inner tubular member 25 which is configured to slidably receive a guidewire 27 suitable for advancement through a patient's body lumen such as the coronary arteries. Lumen 17 extends between distal port 18 and the proximal port 28 which is located about 4 to about 50 cm, preferably about 15 to about 30 cm from the distal port 18. Notch marker 29 is provided to facilitate location of the proximal port 28 under fluoroscopic observation. A mid-balloon marker 30 is provided on the exterior of the inner tubular member 25 for fluoroscopic location of the balloon during the procedure. A distal marker 31 is provided to facilitate fluoroscopic observation of the distal tip 32 during the procedure. The distal extremity of the inner tubular member is tapered at the distal tip 32 of the catheter 10. The exterior surface of the inner tubular member 25 of the distal shaft section 13 is preferably compatible with the material of the balloon 14 and the outer tubular member 24 so that they can be readily bonded by fusion bonding. The presently preferred material is a polyamide elastomer, e.g. a polyether block amide such as PEBAX or Nylon.

The balloon 14 may be formed of suitable compliant, non-compliant or hybrid compliant material, including thermoplastic and thermoelastic polymers depending upon the end use, e.g. dilatation, stent delivery etc. In one embodiment the balloon polymeric material is a relatively compliant polyether block amide such as Pebax 7033 SA01 sold by Elf Atochem. Other materials include Nylon 11 and 12 and Pebax 7233 SA01. Compliant polymeric materials, i.e. compliant within the working expansion of the balloon, which provide a wingless balloon and which have substantially elastic recoil during deflation are also suitable for stent delivery work. Other desirable polymeric materials for balloon manufacture include polyurethanes such as Pellethane 2363-75D from Dow Plastics.

The catheter shaft will generally have the dimensions of conventional dilatation or stent deploying catheters. The length of the catheter 10, measured from the distal end of the adapter 16 to the distal end of the catheter may be about 90 cm to about 150 cm, and is typically about 137 cm. The outer tubular member 24 of the distal section has a length of about 15 cm to about 25 cm, typically about 20 cm, an outer diameter (OD) of about 0.025 in to about 0.045 in (0.6–1.1 mm), preferably about 0.034–0.038 in (0.9–0.96 mm) and an inner diameter (ID) of about 0.02 to about 0.04 in (0.5–1 mm), preferably about 0.028 to about 0.032 in (0.7–0.8 mm). The inner tubular member 25 has a length of about 18 cm to about 40 cm, preferably about 25 to about 30 cm, an OD of about 0.02 to about 0.026 in (0.5–0.7 mm) and an ID of about 0.012 to about 0.022 in (0.3–0.56 mm). The inner and outer tubular members may taper in the distal section to a smaller OD or ID.

The length of the balloon 14 may be about 10 mm to about 50 mm, preferably about 10 mm to about 40 mm. In an expanded state, the balloon diameter is generally about 0.5 mm to about 4.5 mm, typically about 1.5 to about 4 mm. The wall thickness will vary depending upon the burst pressure requirements and the hoop strength of the balloon material.

Figure 4:
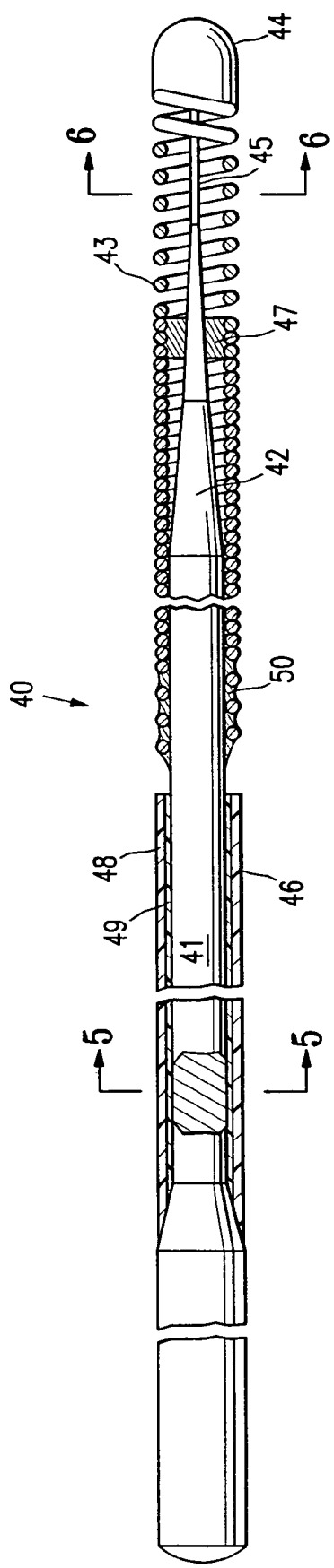
FIG. 4 is schematic, elevational view, partially in section, of a guidewire embodying features of the invention.
Figure 6:
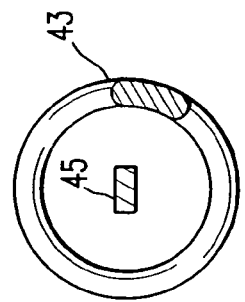
FIG. 6 is a transverse cross sectional view of the guidewire of FIG. 4 taken along lines 6—6.
Figure 5:
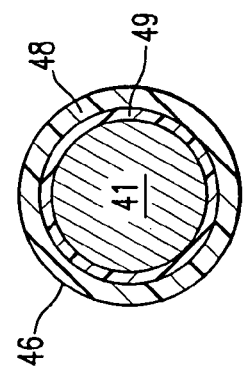
FIG. 5 is a transverse cross sectional view of the guidewire of FIG. 4 taken along lines 5—5.

FIGS. 4–6 illustrate an alternative embodiment, generally directed to a guidewire 40 which includes an elongated core member 41 having a tapered distal member 42. A helical coil 43 is disposed about the distal portion of core 41 and has a rounded plug 44 on the distal end thereof which secures the distal end of the coil 43 to the flattened distal end 45 of the core 41. The coil 43 is secured to the distal member at proximal location 46 and at intermediate location 47 by a suitable solder. Preferably, the most distal section of the helical coil 43 is made of radiopaque metal such as platinum or platinum-nickel alloys to facilitate the fluoroscopic observation while it is disposed within a patient's body.

A portion of core member 41 is covered with jacket 46 that has a two layered structure, preferably formed by coextrusion, with an outer layer 48 being a polymeric material having desirable high strength properties and an inner layer 49 of adhesive polymer. In one current embodiment the outer layer 48 is a polyurethane suitable for coating with a hydrophilic material or a strong, neckable polymer such as Nylon 12 (available from EMS-Chemie (North America) Inc., or high density polyethylene. Outer layer 47 may also comprise a polymer selected for its flexural modulus, inherent lubricity or other desired performance characteristic. Inner layer 49 is formed of a polymer having adhesive properties, which with a current embodiment includes ethylene acrylic acid copolymers (for example, Primacor, available from Dow Plastics) and tie layer resin or functionally modified polyolefins (for example, Plexar, available from Equistar Chemicals.). As used herein, adhesive polymers describe polymers that, once secured to the core member, cannot be detached with reasonable force, without using tools such as a razor blade. Inner layer 49 and core member 41 allows good adhesion between jacket 46 and core member 41, allowing outer layer 48 to be formed from materials such as certain nylons and polyurethanes, for example, that do not adhere well to the guidewire alone. The polymer jacket 46 may extend along a portion or the entire length of the elongated core member 41. The solder securing the coil 43 to the core member 41 and the coil 43 may be covered by the jacket 46. If the coil 43 is covered with the jacket 46 may maintain the exterior surface profile of the coil in order to retain tactile feedback to the physician which such surface provides.

Generally, jacket 46 is drawn over core member 41 at elevated temperatures. Preferably, adhesive inner layer 49 has a melt temperature lower than outer layer 48. This allows the drawing procedure to occur at a temperature at which inner layer 48 melt flows while the outer layer simply deforms in its solid state. Without the inner layer, the outer layer would have to be heated to a greater temperature in order to obtain good adhesion to the guidewire, increasing the chance of breakage during the draw.

It will be apparent from the foregoing that, while particular forms of the invention have been illustrated and described, various modifications can be made without departing from the spirit and scope of the invention. For example, the methods of the invention may be used to adhere a polymer jacket to virtually any intracorporeal member. Moreover, those skilled in the art will recognize that features shown in one embodiment may be utilized in other embodiments.

The particular embodiments shown and described by reference to the figures should not be considered limiting to the invention, and various modifications and combinations of features and embodiments according to this disclosure may be made by those skilled in the art without departing from the scope of this invention. Moreover, use of the terms "device", "member", "element" or "mechanism" and words of similar import herein or in the appending claims shall not invoke the provisions of 35 U.S.C. §112(6) unless specific reference is made to "means" followed by an intended function. Moreover, those skilled in the art will recognize that features shown in one embodiment may be utilized in other embodiments.

What is claimed is:

1. An elongated intracorporeal medical device comprising an elongate shaft having at least a section that is a metallic tubular member with a polymer jacket which is disposed about and secured to at least a portion of the metallic tubular member, the polymer jacket having an outer layer of high strength polymer and an inner layer of an adhesive polymer between and bonding the high strength polymer to the metallic tubular member.

2. The elongated intracorporeal device of claim 1 wherein the inner layer adhesive polymer is selected from the group consisting of ethylene acrylic acid copolymer, functionally modified polyolefins and an ethylene methacrylic acid copolymer.

3. The elongated intracorporeal device of claim 1 wherein the high strength polymer of the outer layer is selected from the group consisting of polyurethane, nylon 12 and a polyether block amide and high density polyethylene.

4. The elongated intracorporeal device of claim 1 wherein the high strength polymer of the outer layer has a melting temperature greater than the melting temperature of the adhesive polymer of the inner layer.

5. The elongated intracorporeal device of claim 1 wherein the outer layer and inner layer are a coextrusion.

6. The elongated intracorporeal device of claim 5 wherein the polymer jacket is necked over the shaft.

* * * * *